(12) United States Patent
Cui et al.

(10) Patent No.: US 10,835,615 B2
(45) Date of Patent: Nov. 17, 2020

(54) SUPRAMOLECULAR HYDROGELS CONTAINING ANGIOTENSIN RECEPTOR BLOCKERS FOR TARGETED TREATMENT OF DIABETIC WOUNDS

(71) Applicant: THE JOHNS HOPKINS UNIVERSITY, Baltimore, MD (US)

(72) Inventors: Honggang Cui, Lutherville-timonium, MD (US); Jeremy D. Walston, Baltimore, MD (US); Peter M. Abadir, Woodstock, MD (US); Ran Lin, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/765,357

(22) PCT Filed: Sep. 30, 2016

(86) PCT No.: PCT/US2016/054736
§ 371 (c)(1),
(2) Date: Apr. 2, 2018

(87) PCT Pub. No.: WO2017/059226
PCT Pub. Date: Apr. 6, 2017

(65) Prior Publication Data
US 2018/0289831 A1 Oct. 11, 2018

Related U.S. Application Data

(60) Provisional application No. 62/236,322, filed on Oct. 2, 2015.

(51) Int. Cl.
| | |
|---|---|
| *A61K 47/65* | (2017.01) |
| *A61K 31/41* | (2006.01) |
| *A61K 9/00* | (2006.01) |
| *A61K 9/06* | (2006.01) |
| *A61K 47/55* | (2017.01) |
| *A61K 47/69* | (2017.01) |
| *A61K 31/4184* | (2006.01) |
| *A61K 31/4178* | (2006.01) |
| *A61K 31/4245* | (2006.01) |
| *A61P 17/02* | (2006.01) |

(52) U.S. Cl.
CPC ............ *A61K 47/65* (2017.08); *A61K 9/0014* (2013.01); *A61K 9/06* (2013.01); *A61K 31/41* (2013.01); *A61K 31/4178* (2013.01); *A61K 31/4184* (2013.01); *A61K 31/4245* (2013.01); *A61K 47/55* (2017.08); *A61K 47/6903* (2017.08); *A61P 17/02* (2018.01)

(58) Field of Classification Search
None
See application file for complete search history.

(56) References Cited

U.S. PATENT DOCUMENTS

| | | | |
|---|---|---|---|
| 2003/0228254 A1* | 12/2003 | Klaveness | A61K 49/0021 424/1.11 |
| 2011/0052674 A1 | 3/2011 | Almirante et al. | |
| 2015/0238465 A1* | 8/2015 | Abadir | G01N 33/566 514/381 |

OTHER PUBLICATIONS

Gabriel, Vincent Ashley, "Transforming growth factor beta and angiotensin in fibrosis and burn injuries." J. Burn Care Res. (2009) 30 p. 471-481.*
Madaghiele, Marta et al; "Polymeric hydrgels for burn wound care: advanced skin wound dressings and regenerative templates." Burns Trama (available Oct. 25, 2014) 2(4) p. 153-161.*
Hoare, Todd R. and Kohane, Daniel S.; "Hydrogels in drug delivery: progess and challenges." Polymer (2008) 49 p. 1993-2007.*
Cui, Honggang et al; "Amino acid sequence in constitutionally isomeric tetrapeptide amphiphiles dictates architecture of one dimensional nanostructures." JACS (20104, published Aug. 2014) 136 p. 12461-12468.*
Bull, Steve R. et al, "Magnetic resonance imaging of self assembled biomaterial scaffolds." Bioconjugate Chem. (2005) 16 p. 1343-1348.*
Nixon, R. M et al, "Valsartan vs. other angiotensin II receptor blockers int he treatment of hypertension: a meta-analytical approach." Int. J. Clin. Pract. (2009) 63(5) p. 766-775.*
Mayo Clinic's web page on psoriasis, https://www.mayoclinic.org/diseases-conditions/psoriasis/symptoms-causes/syc-20355840, downloaded Nov. 13, 2019.*
Bodde, H. E. et al, "Hydrogel patches for transdermal drug delivery; in-vivo water exchange and skin compatibility." J. Pharm. Pharmacol. (1989) 41 p. 152-155).*
Machine translation of JPH03-246299 (1991).*
International Search Report for Application No. PCT/US16/54736 dated Jan. 9, 2017.

* cited by examiner

*Primary Examiner* — Fred H Reynolds
(74) *Attorney, Agent, or Firm* — Taroli, Sundheim, Covell & Tummino LLP

(57) ABSTRACT

The invention described herein provides novel ampiphilic compounds that self-assemble into a hydrogel composition useful for treating wounds, including chronic wounds and diabetic wounds. The compounds of the invention have structural characteristics, such as hydrophilic and hydrophobic moieties, that enable self-assembly into discrete nanostructures, which then entangle to form the hydrogel. Also provided are methods for treating wounds.

10 Claims, 2 Drawing Sheets
Specification includes a Sequence Listing.

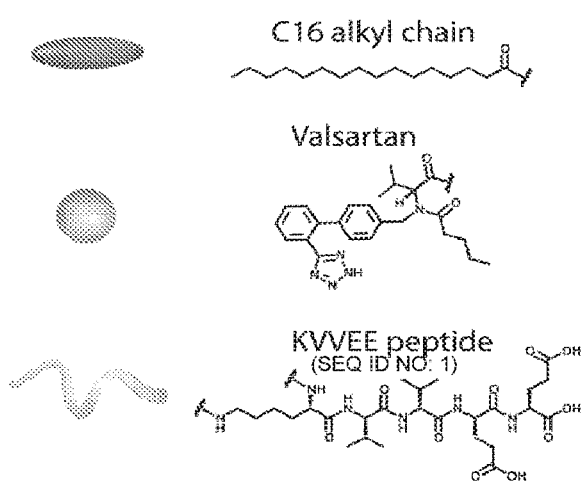
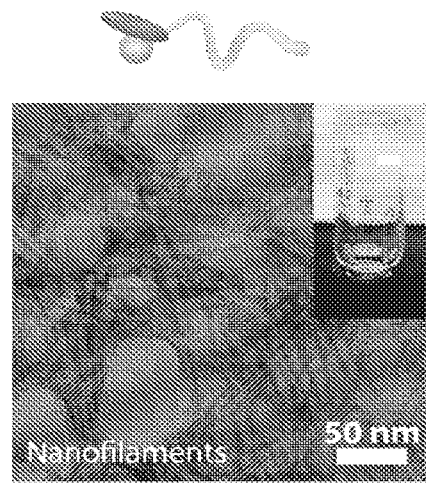
Figure 3a and Figure 3b.
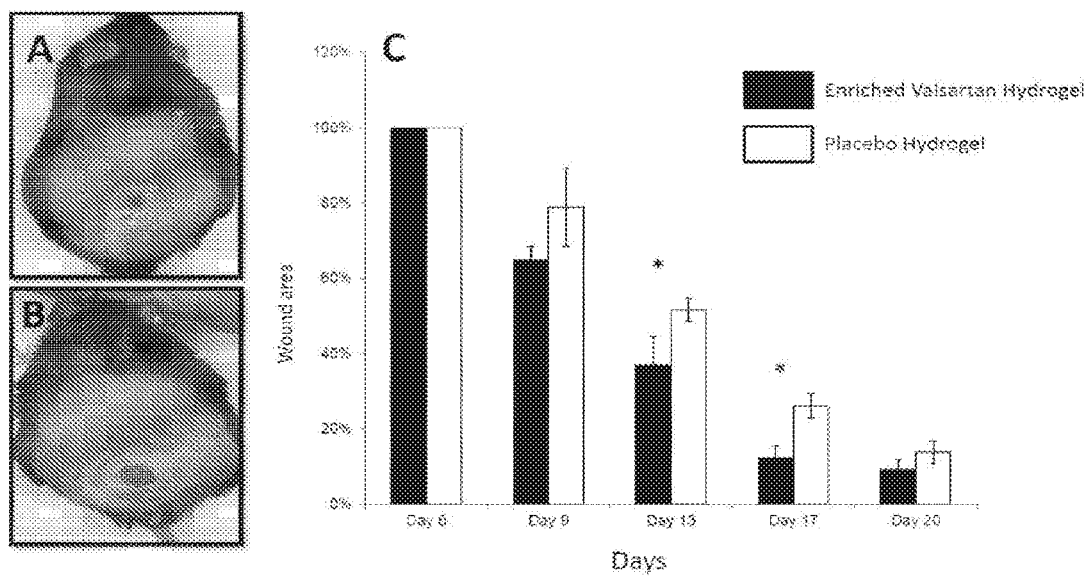
Figure 4.

SUPRAMOLECULAR HYDROGELS CONTAINING ANGIOTENSIN RECEPTOR BLOCKERS FOR TARGETED TREATMENT OF DIABETIC WOUNDS

RELATED APPLICATIONS

This application is the U.S. national phase entry of PCT/US2016/054736, with an international filing date of Sep. 30, 2016, which claims the benefit of U.S. Provisional Application Ser. No. 62/236,322, filed Oct. 2, 2015, the content of which is incorporated herein by reference.

GOVERNMENT SUPPORT

This invention was made with government support under AG021334 and AG043284, awarded by the National Institutes of Health. The government has certain rights in this invention.

SEQUENCE LISTING

The instant application contains a Sequence Listing which has been filed electronically in ASCII format and is hereby incorporated by reference in its entirety. Said ASCII copy, created on Mar. 19, 2020, is named JHU-026949 US PCT ST25.txt and is 1,262 bytes in size.

BACKGROUND

Dysregulation in the renin-angiotensin system (RAS) has been increasingly implicated in abnormal diabetic wound healing. RAS is involved in the inflammatory response, collagen deposition and in tissue-related growth factor (TGF-β) signaling necessary for wound healing. RAS also plays a critical role in mitochondrial homeostasis and mitochondrial energy production necessary for wound repair. In diabetes, with increased AT1R and decreased AT2R expression in diabetic wound healing and in aging, which may play a role in aging skin vulnerability. Indeed, altered dermal AT1R and AT2R ratio is associated with thinning of epidermis, degeneration of collagen, fracture of dermal layer, and atrophy of subcutaneous fat in a diabetic rat. The effect of an angiotensin receptor blocker (AT1R) in a wounded subject can be harmful or beneficial, and is dependent on the stage of wound healing. In particular, previous studies determined that the use of topical angiotensin receptor blockers during the early stage of wound healing (i.e., the inflammation phase) is detrimental and can impair many biological processes critical for wound healing. However, use of these drugs during later stages of wound healing (e.g., proliferative and remodeling stages) can significantly enhance wound healing rate and improve scar quality through effects on TGF-β signaling pathway and mitochondrial bioenergetics. This narrow margin between harm and benefit, in addition to the need for the frequent (e.g., daily) drug administration during the proliferative phase, are major obstacles impeding the therapeutic use of angiotensin receptor blockers in wound healing. There exists a need for compositions that can help control the administration of a locally-applied angiotensin receptor blocker over a sustained period of time and promote wound-healing processes such as neovascularization, cell proliferation and tissue regeneration.

SUMMARY OF INVENTION

The present invention provides compositions and methods for the treatment of wounds.

One aspect of the invention is a compound, comprising a residue of a drug molecule, wherein the drug molecule binds to an angiotensin receptor; and a hydrocarbon moiety; wherein the residue of a drug molecule and the hydrocarbon moiety are covalently linked through a peptide fragment comprising from about 2 to about 20 amino acid residues.

Another aspect of the invention is a supramolecular structure comprising a plurality of compounds of the invention.

Another aspect of the invention is a hydrogel, comprising a plurality of compounds of the invention.

In another aspect, the invention is a hydrogel, comprising a plurality of supramolecular structures of the invention.

In another aspect, the invention provides a method for treating a cutaneous wound, comprising administering to the cutaneous wound in a subject in need thereof a therapeutically effective amount of the hydrogel of the invention.

BRIEF DESCRIPTION OF THE DRAWINGS

FIG. 3a shows three exemplary components of a valsartan-based drug amphiphile (1) the hydrophobic alkyl chain C16, (2) the wound healing drug valsartan, and (3) the β-sheet forming KVVEE peptide (SEQ ID NO:1).

FIG. 3b is a TEM image that shows that mikto-arm dual moiety drug conjugate containing both C16 alkyl chain and valsartan drug residue self-assembles to give long nanofilaments. The inset of FIG. 3b shows a self-supporting hydrogel formed by Val-C16-KVVEE (Val-C16-SEQ ID NO: 1).

FIG. 4 consists of panels A-C, and show representative images from a diabetic mouse treated with enriched valsartan hydrogel (Panel A) and placebo hydrogel (Panel B) on day 13 of wound healing. Planimetric assessment of wound closure rate in diabetic mice is shown in panel C. Data are means±SEM (n=4 animals) *p<0.05.

DETAILED DESCRIPTION OF THE INVENTION

Compounds and Compositions

Figure 2:
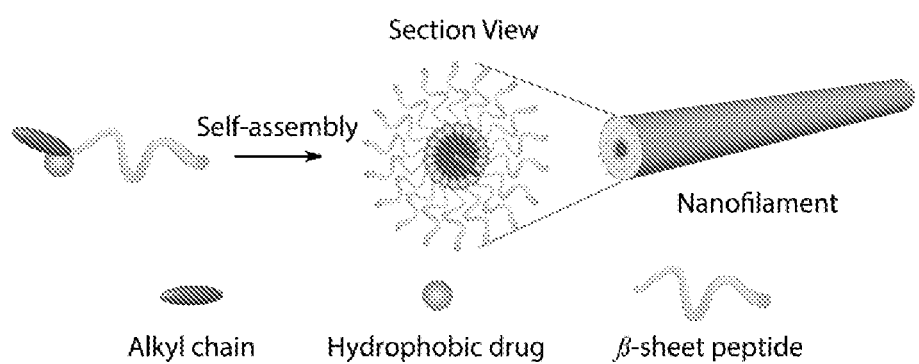
FIG. 2 illustrates the synthetic design of the compounds of the invention, and also demonstrates their assembly into supermolecular structures. Three structural elements are pictured: Element 1 is a short peptide capable of forming intermolecular hydrogen bonds, leading to β-sheet structures. Element 2 is a linear hydrocarbon of various lengths, and Element 3 is a therapeutic angiotensin receptor blocker. The overall hydrophilic nature of Element 1 and the hydrophobic nature of Element 2 enables assembly of these compounds into discrete nanostructures.

The present invention is based on the surprising discovery that a hydrogel formulation enriched with an angiotensin receptor blocker enhanced wound healing in animals as compared to animals treated with placebo. The hydrogel comprises a plurality of compounds that contain a therapeutic agent moiety and hydrophobic and hydrophilic elements that give structure to the composition. The general design for the drug ampiphiles of the invention is illustrated in FIG. 2.

Accordingly, in certain embodiments, the invention provides a compound, comprising:

a residue of a drug molecule, wherein the drug molecule binds to an angiotensin receptor; and a hydrocarbon moiety;

wherein the residue of a drug molecule and the hydrocarbon moiety are covalently linked through a peptide fragment comprising from about 2 to about 20 amino acid residues.

In certain embodiments, the compound of the invention, in use, releases or dissociates that residue of the drug molecule. Such a dissociate or release can occur, for example, via hydrolysis of one or more bonds under certain physiological conditions. Accordingly, in certain embodiments, the peptide fragment is covalently linked to the residue of the drug molecule through one or more covalent bonds, wherein at least one bond is selected from amide, carbonate, carbamate, ester, ether, disulfide, sulfonate, and sulfamate.

In certain embodiments, the peptide fragment is covalently linked to the hydrocarbon moiety through one or more covalent bonds, wherein at least one bond is selected from amide, carbonate, carbamate, ester, ether, sulfonate, and sulfamate. Preferably, at least one bond linking the peptide fragment to the hydrocarbon moiety is an amide bond.

In certain embodiments, the peptide fragment comprises from about 4 to about 10 amino acid residues.

The peptide fragment is an element of the compound that can provide structure to the compound itself, discrete supramolecular structures comprising the compound of the invention, or the hydrogel composition of the invention as described herein. Accordingly, in certain embodiments, the peptide fragment is capable of forming intramolecular hydrogen bonds. In further embodiments, the peptide fragment is capable of forming a beta sheet secondary protein structure. The use of β-sheet-forming peptides leads to the formation of filamentous nanostructures.

In certain embodiments, the residue of a drug molecule is bound to the N-terminus of the peptide fragment, and the hydrocarbon moiety is bound to a side chain of an amino acid residue of the peptide fragment. In alternative embodiments, the residue of a drug molecule is bound to a side chain of an amino acid residue of the peptide fragment, and the hydrocarbon moiety is bound to the N-terminus of the peptide fragment.

Accordingly, in certain embodiments, the peptide fragment comprises at least one amino acid residue that has a substitutable position on its side chain. In certain embodiments, the substitutable position is an amino group, a hydroxyl group, or a thiol group.

In certain embodiments, the peptide fragment comprises at least one amino acid residue selected from Lys, Arg, Asp, Glu, Gln, Asn, Thr, Ser, Cys, Sec, and Pro. In certain embodiments, the peptide fragment comprises a Lys residue. Lysine, for example, contains a substitutable side chain that can covalently bond to the residue of the drug molecule or the hydrocarbon moiety.

In certain embodiments, the peptide fragment comprises an amino acid sequence having at least 50%, 60%, 70%, 80%, or 90% sequence homology to Lys-Val-Val-Glu-Glu (SEQ ID NO: 1). In certain embodiments, the amino acid sequence is Lys-Val-Val-Glu-Glu (SEQ ID NO: 1).

In certain embodiments, the peptide fragment comprises an amino acid sequence having at least 50%, 60%, 70%, 80%, or 90% sequence homology to Val-Val-Arg-Gly-Asp-Ser (SEQ ID NO: 2). In certain embodiments, the amino acid sequence is Val-Val-Arg-Gly-Asp-Ser (SEQ ID NO: 2).

In certain embodiments, the drug molecule binds to an $AT_1$-type receptor and/or an $AT_2$-type receptor.

In certain embodiments, the drug molecule is an angiotensin receptor blocker.

In certain embodiments, the drug molecule is selected from the group consisting of valsartan, telmisartan, losartan, irbesartan, azilsartan, olmesartan, candesartan, and ephrosartan. In certain preferred embodiments, the drug molecule is valsartan.

The hydrocarbon moiety in the compound of the invention may be fully saturated or can be fully or partially unsaturated; that is, it may contain one or more carbon-carbon double or triple bonds. The hydrocarbon moiety can be linear or branched; preferably it is linear.

In certain embodiments, the hydrocarbon moiety is ($C_3$-$C_{25}$) linear alkyl. In certain embodiments, the hydrocarbon moiety is ($C_8$-$C_{21}$) linear alkyl. In certain embodiments, the hydrocarbon moiety is ($C_{15}$) linear alkyl.

In certain embodiments, the residue of the drug molecule and the hydrocarbon moiety are covalently linked to the peptide fragment at the same amino acid residue of the peptide fragment.

In certain embodiments, the residue of the drug molecule and the hydrocarbon moiety are covalently linked to the peptide fragment at different amino acid residues of the peptide fragment.

In certain embodiments of the compound of the invention, the C-terminus of the peptide fragment is covalently bound to a cell targeting peptide moiety, a cell-penetrating peptide moiety, a mitochondria-targeting peptide moiety, fluorophore, or a tissue-penetrating peptide moiety.

In certain embodiments, the C-terminus of the peptide fragment can be the acid (i.e., the carboxylic acid, —C(O)OH), an optionally substituted amide (e.g., —C(O)NH$_2$, —C(O)NMe$_2$), or an ester (e.g., —C(O)OMe). In certain embodiments, the C-terminus of the peptide fragment is an amine.

In certain embodiments, the peptide fragment is linked to the residue of the drug molecule through a linking moiety.

In certain embodiments, the linking moiety is an amide, carbonate, carbamate, ester, ether, disulfide, sulfonate, or sulfamate linking moiety. In certain embodiments, the linking moiety is a disulfide linking moiety.

In certain embodiments, one or more covalent bonds in the linking moiety are cleaved in a cell. Exemplary enzymes that can cleave or degrade the linking moiety include cathepsins or matrilysins.

In certain embodiments, one or more covalent bonds linking the residue of the drug molecule to the peptide fragment are cleaved in use, e.g., in a cell, in an extracellular matrix, on contact with a tissue or with wounded tissue.

In certain embodiments, the compound of the invention has the structure of formula (I):

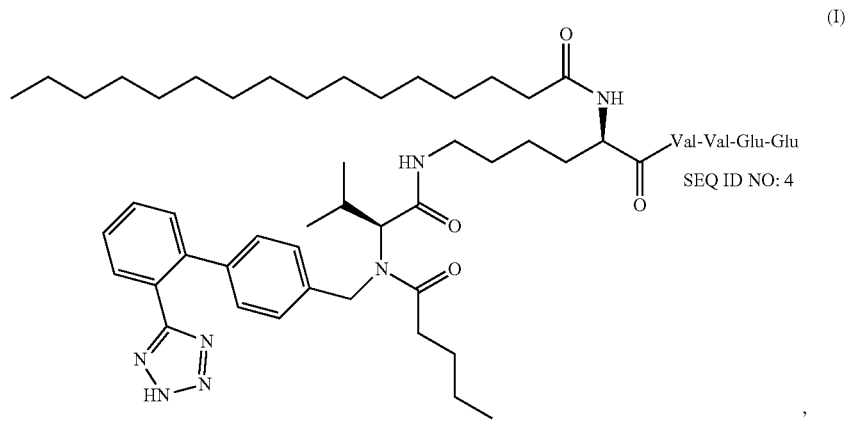

(I)

or a pharmaceutically acceptable salt thereof.

In certain embodiments, the residue of the drug molecule that is incorporated into the compounds of the invention is derived from a bioactive drug compound. A drug residue may be related to the parent structure of the bioactive drug compounds by chemical modification (e.g., substitution) of the parent structure. In example embodiments, a parent structure can be modified by a linking moiety that effectively attaches the drug residue to a scaffold, as described herein.

Modifications of a bioactive drug compound include substitution, truncation, stereocenter inversion, isomerization, or hybridization change. In certain embodiments, a bioactive drug compound is substituted at any substitutable position, including a heteroatom (e.g., O, N, S, Se, P), a hydrogen-bearing $sp^2$-hybridized carbon, or a hydrogen-bearing $sp^3$-hybridized CH. Exemplary sites of truncation in a parent drug compound can include ester, amide, ether, carbonate, and carbamate moieties.

A person of ordinary skill in the art would appreciate that a bioactive drug compound can be incorporated as a drug residue into the compounds of the invention in any one of a variety of spatial orientations, and at any one of a variety of substitutable positions, as described herein. A person of ordinary skill in the art can readily synthesize a number of such compounds in order to determine which orientations and connectivities exhibit acceptable biological activity for a given application. In example embodiments, a compound with a drug residue having appropriate orientation and connectivity retains the type of biological activity of the parent bioactive drug compound, though the activity of the compound bearing the drug residue may be stronger or weaker than that of the parent bioactive drug compound. In certain embodiments, a suitable orientation and connectivity is determined when the drug residue exhibits at least 99%, 98%, 95%, 90%, 85%, 80%, 75% 70%, 65%, 60%, 55%, or 50% of the biological activity of parent compound.

In certain embodiments, compounds of the invention may have one or more chiral centers, whether in the drug residue, the peptide fragment, or the hydrocarbon moiety. In certain such embodiments, compounds of the invention may be enriched in one or more diastereomers or one or more enantiomers. For example, a compound of the invention may have greater than 30% de, 40% de, 50% de, 60% de, 70% de, 80% de, 90% de, or even 95% or greater de. A diastereo-enriched composition or mixture may comprise, for example, at least 60 mol percent of one diastereomer, or more preferably at least 75, 90, 95, or even 99 mol percent of one diastereomer. In certain embodiments, the compound enriched in one diastereomer is substantially free of the other diastereomers, wherein substantially free means that the other diastereomers make up less than 10%, or less than 5%, or less than 4%, or less than 3%, or less than 2%, or less than 1% as compared to the amount of the primary diastereomer, e.g., in the composition or compound mixture. For example, if a composition or compound mixture contains 98 grams of a first diastereomer and 2 grams of a second diastereomer, it would be said to contain 98 mol percent of the first diastereomer and only 2% of the second diastereomer. In certain embodiments, a compound of the invention may have greater than 30% ee, 40% ee, 50% ee, 60% ee, 70% ee, 80% ee, 90% ee, or even 95% or greater ee. An enantio-enriched composition or mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the other enantiomer makes up less than 10%, or less than 5%, or less than 4%, or less than 3%, or less than 2%, or less than 1% as compared to the amount of the primary enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer. The compounds of the invention may also be racemic mixtures of enantiomers.

Figure 1:
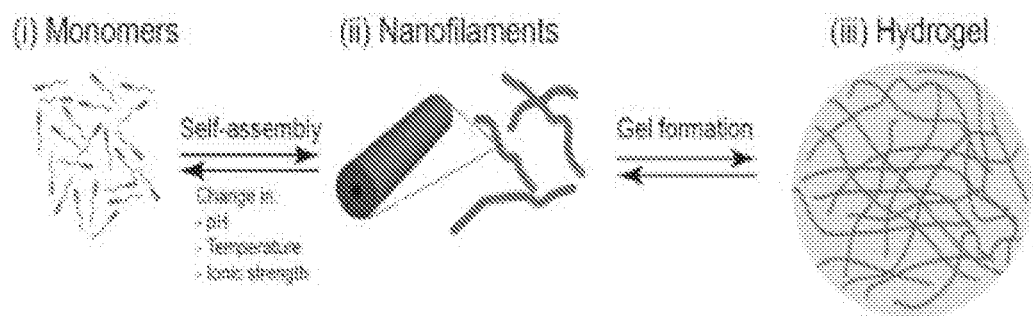
FIG. 1 depicts the self-assembly of amphiphilic peptide monomers into nanofilaments that can enmesh to form hydrogels. The process is reversible and tunable by various stimuli. The low viscosity of the monomeric state offers great flexibility in handling and processing. The resultant hydrogels can be used to directly carry hydrophilic objects (proteins, peptides, or cells) for local delivery similar to other hydrogel systems made of hydrophilic covalent polymers.

FIG. 1 illustrates the basic design principle behind the rationally designed small molecules of the invention, which assemble into nanofilaments that can entangle to form hydrogels.

In certain embodiments, a plurality of the compound of the invention self-assemble into a supermolecule structure, e.g., a nanofiber, in aqueous solution. The aqueous solution can be water or phosphate-buffered saline.

In certain embodiments, the invention relates to a supramolecular structure, comprising a plurality of compounds of as described herein.

In certain embodiments, the supramolecular structure is in the form of a nanofilament. The nanofilament may be semi-flexible.

In certain embodiments, a plurality of the supramolecular structures entangle in aqueous solution, forming a hydrogel.

In certain embodiments, a plurality of the supramolecular structures form a hydrogel in aqueous solution at concentrations greater than about 0.3%, about 0.4%, about 0.5%, about 0.6%, or about 0.7% by weight.

Hydrogel Compositions

Hydrogels are advantageous for wound healing in part because they maintain the moist environment necessary for wound healing. Further advantages include their biocompatibility and non-adherent nature, which can reduce patient discomfort. The hydrogels of the invention promote important biological processes (e.g. neovascularization, cell proliferation and tissue regeneration) critical for an enhanced wound repair.

The creation of hydrogels with built-in healing and anti-inflammatory properties could greatly simplify and extend the usage of these compositions. Furthermore, the permeable nature of hydrogels to water soluble molecules opens up the possibility of delivering supplemental aids for healing, such as growth factors like epidermal growth factor (EGF) and granulocyte-macrophage colony-stimulating factor (GM-CSF), and vitamins. Formulations with other biopolymers, such as hyaluronic acid (HA), may give rise to hydrogels with very different mechanical properties, possessing the potential to yield very robust yet flexible sheets that would not require any secondary dressings.

The invention provides scaffolding hydrogels enriched with a renin angiotensin receptor blocker, such as valsartan, that address an unmet need for controlling the onset and the rate of delivery of locally applied renin angiotensin receptor blocker to healing wound tissue over a long period of time. These hydrogels can slowly release the bioactive compound, accelerating wound healing.

The release rate of the bioactive compound or drug residue from the self-assembled nanofilaments can be tuned by choice of various chemical linkers that bridge the drug residue and the peptide segment, and also by the dissociation kinetics of the assembled nanostructures. For example, delayed release of valsartan (e.g., to bypass the first inflammatory phase) can be achieved by using a disulfide chemical linker that connects valsartan to the peptide segment. This linker is stable in the physiological environment but will break down after the valsartan conjugate enters cells and encounters the reducing agent glutathione within cytosol.

Accordingly, the invention also provides hydrogel compositions, comprising a plurality of compounds of the invention, as described herein, and water.

In certain embodiments, the hydrogel of the invention comprises a plurality of supramolecular structures of the invention, as described herein, and water.

In certain embodiments, the hydrogel is formed from a solution of a plurality of compounds of the invention in an aqueous solution. The aqueous solution may be, for example, water or phosphate-buffered saline.

In certain embodiments, the compound is present in the hydrogel in an amount of about 0.25% to about 10%, about 0.3% to about 5%, about 0.4% to about 5%, about 0.5% to about 4.5%, about 0.5% to about 4%, about 0.5% to about 3.5%, about 0.5% to about 3%, about 0.5% to about 2.5%, about 0.5% to about 2%, about 0.5% to about 1.5%, or about 1% by weight.

The sustained release of a drug residue can result from the supramolecular nature of the drug filaments. In fact, it has been found that at higher concentrations, the chemically modified drug is slowly released out over a long period (Cheetham, A. G.; Zhang, P.; Lin, Y.-A.; Lock, L. L.; Cui, H., Supramolecular nanostructures formed by anticancer drug assembly, Journal of the American Chemical Society, 2013, 135 (8), 2907-2910). In other embodiments, to manipuate the release rate, a filler self-assembling peptide conjugate may be used that has structural features substantially similar to the hydrocarbon-drug-peptide conjugate described herein, except lacks the drug residue. Such a filler peptide can be mixed with the drug residue-containing conjugate (e.g., a valsartan conjugate) at different mixing ratios to tune the ultimate release rate of the drug residue from the hydrogels.

In certain embodiments, the hydrogel further comprises a plurality of a second compound, wherein the second compound comprises a peptide fragment covalently linked to a hydrocarbon moiety. In certain embodiments, a second compound is substantially similar to a compound of the invention, except that it lacks a residue of a drug compound, or other bioactive component. In certain embodiments, the second compound acts as a filler agent in the hydrogel. The ratio of the second compound/filler agent to the compound containing the bioactive moiety can be tuned to achieve a desired administration profile for the hydrogel.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, the aqueous solution is pyrogen-free, or substantially pyrogen-free. The excipients can be chosen, for example, to effect delayed release of an agent or to selectively target one or more cells, tissues or organs. The hydrogel composition is suitable for topical administration, and can also be present in a transdermal delivery system, e.g., a skin patch, or in an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical hydrogel composition (preparation) can be administered to a subject by any of a number of routes of administration including, for example, absorption through the oral mucosa (e.g., sublingually); anally, rectally or vaginally (for example, as a pessary, cream or foam); transdermally (for example as a patch applied to the skin); and topically (for example, as a cream, ointment or spray applied to the skin, or as an eye drop). In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, and then, if necessary, shaping the product.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Dosage forms for the topical administration include powders, sprays, ointments, pastes, creams, lotions, gels, hydrogels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In another aspect, the invention provides pharmaceutical compositions of the compounds described herein, optionally in admixture with one or more pharmaceutically acceptable excipients. Preferably, the compositions are suitable for topical administration.

In yet another aspect, the invention provides methods for administering the compounds and compositions described herein, e.g., for the treatment of a cutaneous wound in a subject in need thereof.

Compounds of any of the structures described herein and any composition of these compounds may be used in the manufacture of medicaments for the treatment of any diseases or conditions disclosed herein.

Methods of Treatment

Wounds are among the most common, most painful and most debilitating consequences of diabetes, and they are an important portal for bacterial tissue infections that often lead to amputations, sepsis and ultimately mortality. Although there are multiple approaches at present to wound care, most are focused on treating infections and on debridement of necrotic tissue with few agents targeted at specific stages or at specific biological pathways in wound healing. The methods provided herein target the renin angiotensin system (RAS) specifically in the proliferative/remodeling phase of wound healing, which is often dysregulated in those with diabetes. This is potentially significant in that it could not only result in a breakthrough in the targeting of specific biological abnormalities at specific time points in diabetic wound healing, but allow for a better understanding of the biological pathways that disrupt wound repair in diabetes. Our novel approach utilizes the biological knowledge of the timing of necessary early engagement of RAS in the inflammation and early proliferation phases, the decreasing RAS signaling later in wound healing, and the dysregulation of RAS in diabetes. Because the topical formulations described herein targets a local skin renin angiotensin system rather than a systemic renin angiotensin system, this therapy can potentially be used in the patients most at risk for wound development and recurrent wound breakdown, i.e., those with advanced diabetes, progressive renal failure, and cardio-vascular disease.

The invention also provides methods of treating a cutaneous wound, comprising administering to the cutaneous wound in a subject in need thereof a therapeutically effective amount of the hydrogel of the invention.

In certain embodiments, the cutaneous wound is a chronic wound.

In certain embodiments, the cutaneous wound is a diabetic skin ulcer.

In certain embodiments, the cutaneous wound is an ulcer associated with aging skin.

In certain embodiments, the wound is a burn, an electrical injury, a radiation injury, a sunburn, a gun shot injury, an explosives injury, a post-surgical wound, a keloid, scar tissue, psoriasis, a superficial dermatologic resurfacing, or a skin lesion due to an inflammatory condition.

In certain embodiments, the cutaneous wound is in a tissue associated with an upregulation in angiotensin II type 1 receptors.

Administration of the hydrogel of the invention can be topical. Alternatively, administration is buccal administration.

In certain embodiments, the pharmaceutical composition is administered at least 3 days, at least 4 days, at least 5 days, or at least 6 days after wounding. For example, the hydrogel composition of the invention may be administered to a patient after the inflammatory phase of wound healing has passed. The hydrogel composition may be administered to the patient in the proliferative/remodeling phase of wound healing.

In certain embodiments, the subject is a mammal, for example, a human.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

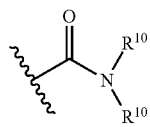

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

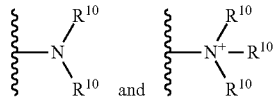

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

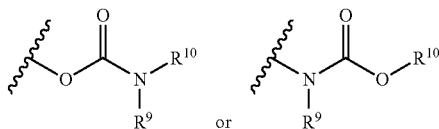

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

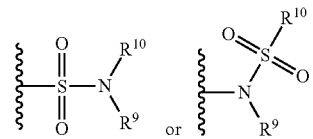

wherein R⁹ and R¹⁰ independently represents hydrogen or hydrocarbyl, such as alkyl, or R⁹ and R¹⁰ taken together with the intervening atom(s) complete a heterocycle having from 4 to 8 atoms in the ring structure.

The term "sulfoxide" is art-recognized and refers to the group —S(O)—R¹⁰, wherein R¹⁰ represents a hydrocarbyl.

The term "sulfonate" is art-recognized and refers to the group SO₃H, or a pharmaceutically acceptable salt thereof.

The term "sulfone" is art-recognized and refers to the group —S(O)₂—R¹⁰, wherein R¹⁰ represents a hydrocarbyl.

The term "thioalkyl", as used herein, refers to an alkyl group substituted with a thiol group.

The term "thioester", as used herein, refers to a group —C(O)SR¹⁰ or —SC(O)R¹⁰ wherein R¹⁰ represents a hydrocarbyl.

The term "thioether", as used herein, is equivalent to an ether, wherein the oxygen is replaced with a sulfur.

The term "urea" is art-recognized and may be represented by the general formula

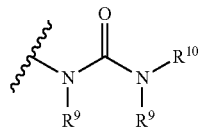

wherein R⁹ and R¹⁰ independently represent hydrogen or a hydrocarbyl, such as alkyl, or either occurrence of R⁹ taken together with R¹⁰ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The term "masking moiety" as used herein, refers to the chemical moiety that is a covalently bound modification of a pharmacophore that renders the compounds of the present invention to which it is attached prodrugs. A masking moiety is cleavable under, for example, acidic conditions, basic conditions, or physiologic conditions. When the masking moiety is cleaved, the prodrugs are converted to the therapeutically active agents of the present invention. Esters and carbonates can be used to mask hydroxyls, carbamates and amides can be used to mask amines, carboxyls can be masked as esters, etc., and in certain embodiments the precise masking moiety can be selected to be cleaved under conditions particular to a region of the digestive tract. For example, an amine or hydroxyl can be acylated by a 4-aminobutanoyl group, to form a prodrug that can be administered as a salt of the amine. In the acidic conditions of the stomach, the amino group will remain protonated, masking its nucleophilicity. In the more basic conditions of the small intestines, the ammonium group will be deprotonated, revealing the nucleophilic amine, which can nucleophilicly attack the amide or ester formed by the butanoyl group, ultimately revealing the amide or ester with the concomitant release of the protecting group as a lactam.

In certain embodiments, the invention relates to a method for conducting a pharmaceutical business, by manufacturing a formulation of a compound of the invention, or a kit as described herein, and marketing to healthcare providers the benefits of using the formulation or kit for treating or preventing any of the diseases or conditions as described herein.

In certain embodiments, the invention relates to a method for conducting a pharmaceutical business, by providing a distribution network for selling a formulation of a compound of the invention, or kit as described herein, and providing instruction material to patients or physicians for using the formulation for treating or preventing any of the diseases or conditions as described herein.

In certain embodiments, the invention comprises a method for conducting a pharmaceutical business, by determining an appropriate formulation and dosage of a compound of the invention for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the invention relates to a method for conducting a pharmaceutical business by determining an appropriate formulation and dosage of a compound of the invention for treating or preventing any of the disease or conditions as described herein, and licensing, to a third party, the rights for further development and sale of the formulation.

EXAMPLES

Example 1. Exemplary Valsartan Amphiphile

A valsartan amphiphile was synthesized using palmitic acid (C16) as the hydrophobic moiety (Element 2), a β-sheet forming peptide sequence KVVEE (SEQ ID NO:1) as Element 1, and the antiotensin receptor blocker valsartan as Element 3 (FIG. 3a). The three elements are linked together using lysine as the junction. The synthesis was done using solid phase peptide synthesis protocol and the compound was purified using reverse HPLC and the expected molecular weight was confirmed by MALDI.

In pure water or PBS, the valsartan amphiphile sponstaneously associated into filaments, as visualized in FIG. 3b by transmission electron microscopy (TEM). TEM reveals that these filaments are approximately 10 nm in diameter and tens of micrometers long. At higher concentrations (typically above 0.5% by weight), the valsartan filaments will entangle into a self-supporting gel.

The peptide AcK(Mtt)VVEE-OH (AcK(Mtt)(SEQ ID NO: 6)-OH) was synthesized using AAPPTEC Focus XC synthesizer via standard Fmoc-solid phase technique. Fmoc groups were deprotected using 20% 4-methylpiperidine in DMF, and amino acid/HBTU/DIEA (4/3.98/6) was applied for coupling. Side chain Mtt group on lysine was deprotected by TFA/TIS/DCM (1/5/94), and valsartan/HBTU/DIEA (4/3.98/6) was applied for coupling. The N-terminal amine was deprotected using 20% 4-methylpiperidine in DMF manually and C16 tail was conjugated by reacting with C16/HBTU/DIEA (4/3.98/6). The finished conjugate was cleaved from the resin with TFA/TIS/water (92.5/5/2.5) solution. The conjugate was confirmed by MALDI-TOFMS.

Example 2. Wound Closure Experiments

The wound healing experiments discussed herein focus on revascularization, histology, and molecular measurements. After wounding, mice were randomly assigned with daily valsartan 1% gel, one time valsartan hydrogel and placebo gel (i.e., without the valsartan moiety). The mice were monitored daily for health status, and measurements of the wound were taken and recorded every other day until all wounds were completely closed. Wound closure measurements, tensile strength measurements and histology study were performed to collect morbidity and mortality information on a daily basis from the time of wounding.

Animal Testing:

The efficacy of 1% Valsartan enriched scaffold was demonstrated as compared to regular placebo gel in a diabetic mouse wound healing model through determining the difference in time to closure of a standardized 8 mm back wound.

Design Overview:

8 week old BKS.Cg-m+/+Lepr$^{db}$/J (dbdb) female mice were utilized for these studies. After one week of equilibration, full thickness 8 mm wound were created on the dorsum aspect of each mouse. After wounding, mice were randomly assigned to a group with a treatment regimen of (1) one time valsartan hydrogel treatment (applied immediately after wounding) or (2) placebo hydrogel group, then the mice were placed in individual cages. Topical treatments (valsartan hydrogel or placebo hydrogel) were applied directly to the wound using an automated dosing dispenser by the same technician, and sterile gauze was utilized to evenly distribute the ointment across the wound. A wound chamber ensuree that topical gel staye in place. The mice were monitored daily for health status, and measurements of the wound were taken and recorded every other day by 3 technicians blinded to treatment groups until all wounds were completely closed.

Methods:

i. Wound closure measurements were taken every other day by trained technicians or investigators using 2 dimensional planimetric assessment of wound closure. Each animal was placed in Mouse Restrainer (Plas Labs, Lansing, Mich.) and outline of the non-epithelialized area of the healing excisional wounds was traced using digital photography.

Data Analysis:

To analyze the primary outcome, time to wound closure, we applied Fine and Gray's semiparametric proportional subdistributional hazards model by treating death before wound closure as a competing risk rather than a censoring event as in the conventional Cox model. Specifically, we estimated the cumulative incidence functions for wound closure, conditioned on being alive, as well as death before wound closure for each treatment dose and compare them with those of the placebo. We used one-way ANOVA to compare the means of tensile strength for the different doses. We will use repeated measures ANOVA to assess differences in blood pressure by treatment and time.

Results:

The results demonstrate that a single application of valsartan-enriched hydrogel significantly enhanced wound healing as compared to placebo treated animals (FIG. 4).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A method for treating a cutaneous wound, comprising:
administering to the cutaneous wound in a subject in need thereof a therapeutically effective amount of a hydrogel comprising water and a compound wherein the compound comprises
a residue of a drug molecule, wherein the drug molecule binds to an angiotensin receptor; and
a hydrocarbon moiety;
wherein the residue of a drug molecule and the hydrocarbon moiety are covalently linked through a peptide fragment wherein the peptide fragment consists of the amino acid sequence Val-Val-Arg-Gly-Asp-Ser (SEQ ID NO:2).

2. The method of claim 1, wherein the cutaneous wound is a chronic wound.

3. The method of claim 1, wherein the cutaneous wound is a diabetic skin ulcer.

4. The method of claim 1, wherein the cutaneous wound is an ulcer.

5. The method of claim 1, wherein the wound is a burn, an electrical injury, a radiation injury, a sunburn, a gun shot injury, an explosives injury, a post-surgical wound, and a psoriasis wound.

6. The method of claim 1, wherein the cutaneous wound is in a tissue associated with an upregulation in angiotensin II type 1 receptors.

7. The method of claim 1, wherein the step of administering is transdermal administration.

8. The method of claim 1, wherein the pharmaceutical composition is administered at least 3 days after wounding.

9. The method of claim 1, wherein the subject is a mammal.

10. The method of claim 9, wherein the subject is a human.

* * * * *

SEQUENCE LISTING

<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Lys Val Val Glu Glu
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Val Val Arg Gly Asp Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Lys Val Val Glu Glu
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Val Val Glu Glu
1

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Lys Val Val Glu Glu
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 6

Val Val Glu Glu
1
```